United States Patent [19]

Grady et al.

[11] 4,365,343
[45] Dec. 21, 1982

[54] COUNTERWEIGHTED X-RAY TUBE

[75] Inventors: John K. Grady, Lincoln; David B. Rice, Cambridge; Paul G. Rice, Lincoln, all of Mass.

[73] Assignee: XRE Corporation, Concord, Mass.

[21] Appl. No.: 203,963

[22] Filed: Nov. 4, 1980

[51] Int. Cl.³ ............................................ G03B 41/16
[52] U.S. Cl. ................................. 378/181; 378/189; 378/197
[58] Field of Search ............... 250/522, 523, 525, 490, 250/444, 445 R, 446, 447, 448, 449, 468, 521

[56] References Cited
U.S. PATENT DOCUMENTS 3,803,417  4/1974  Kok ..................................... 250/447
3,803,418  4/1974  Holstrom ........................... 250/320
3,892,967  7/1975  Grady ................................. 250/447

*Primary Examiner*—Craig E. Church
*Attorney, Agent, or Firm*—James H. Grover

[57] ABSTRACT

X-ray apparatus comprises a U-shaped support having two hollow, horizontal arms. On the end of one arm is mounted an X-ray tube and on the other an X-radiation receptor both guided for movement on a radiation axis.

A counterweight within one hollow, horizontal arm is guided for movement parallel to the X-ray tube, transversely of the arm. To counterbalance the X-ray tube a lever attached to the tube has sliding pivots at a fulcrum and the counterweight allowing the lever arm to change its length without changing the leverage ratio.

8 Claims, 3 Drawing Figures

U.S. Patent    Dec. 21, 1982    4,365,343

COUNTERWEIGHTED X-RAY TUBE

BACKGROUND OF THE INVENTION

This invention relates to X-ray apparatus in which the X-radiation tube and the image intensifier or other radiation receptor are mounted at the ends of two parallel arms of a generally U-shaped support such as is shown in U.S. Pat. No. 3,892,967. The two radiation means are optically aligned on a common radiation axis. In radiological examination of a subject the U-shaped support is turned in a bearing about a rotational axis parallel to the arms on which the X-ray tube and radiation receptor are mounted and through which the radiation axis passes. It is necessary that the rotating assembly of U-shaped support and radiation source and receptor be kept in balance with respect to the rotational axis to reduce bearing friction, to allow the assembly to rest motionless in equilibrium, and also to permit manual rotation of the assembly. On the other hand it is desirable to adjust the X-ray tube along the radiation axis toward and away from the rotational axis which would destroy the equilibrium of the assembly unless adjustment of the X-ray tube weight is compensated by adjustable counterweighting.

Adjustable counterweighting may be achieved by moving sliding weights on cables or the like as shown in the aforementioned patent. However, if both the radiation source and receptor are to be adjusted, there may be insufficient space for the counterbalancing system on or in the arms of the U-shaped support.

Accordingly it is the object of the present invention to provide a counterbalancing system which requires a minimum of space and allows counterbalancing of both the radiation source and the radiation receptor.

SUMMARY OF THE INVENTION

According to the invention radiological apparatus comprises a support; and radiation source means and radiation receptor means at spaced positions on the support for examination of a subject at a location therebetween, the source and receptor means having a common radiation axis extending through the subject location, and each means being mounted on the support to move along the radiation axis; wherein the support includes an arm extending to one radiation means toward the radiation axis; means on the arm guiding the radiation means along the radiation axis; fulcrum means on the arm; a lever pivoted on the fulcrum means and pivotally attached at one end to the radiation means; and a counterweight guided on the arm and engaging the other end of the lever to counterbalance the radiation means.

Further according to the invention the arm is hollow and the counterweight is contained within the arm and guided transversely of the arm.

DRAWING

DESCRIPTION

Figure 1:
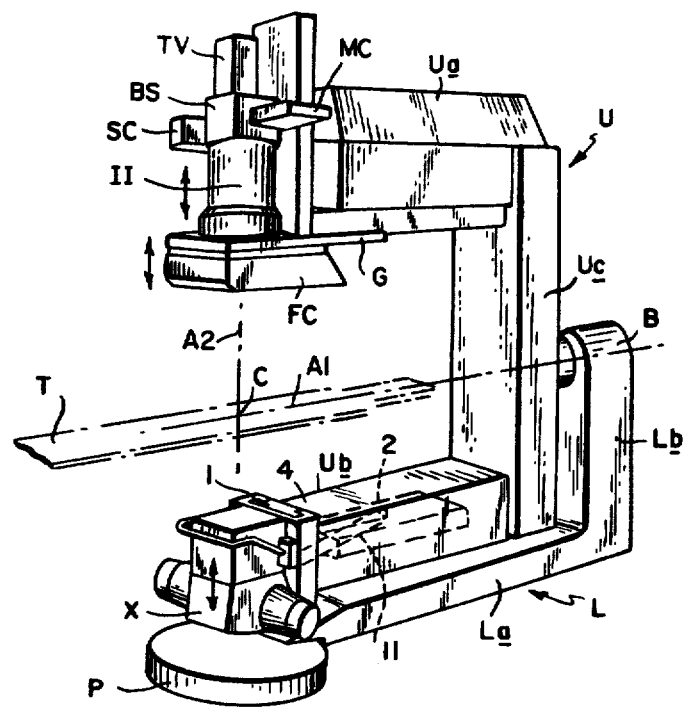
FIG. 1 is an isometric view of radiological apparatus having a counter balancing system according to the invention.
Figure 2:
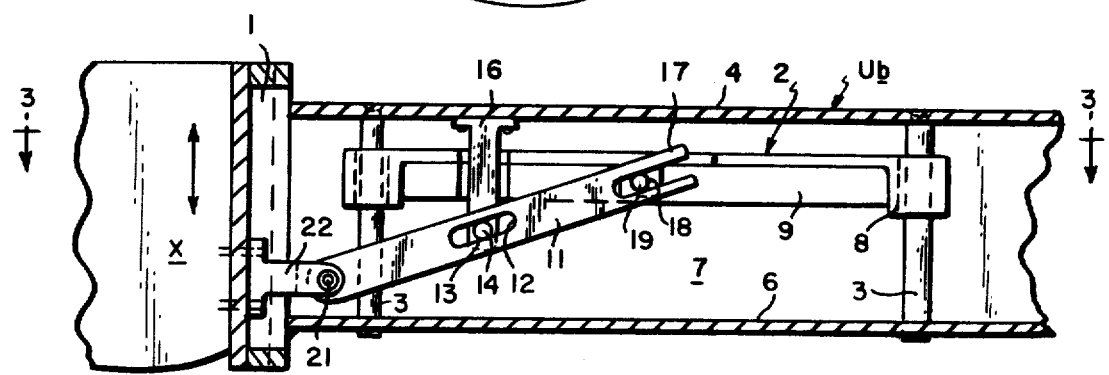
FIG. 2 is a side section of the counter balancing system.
Figure 3:
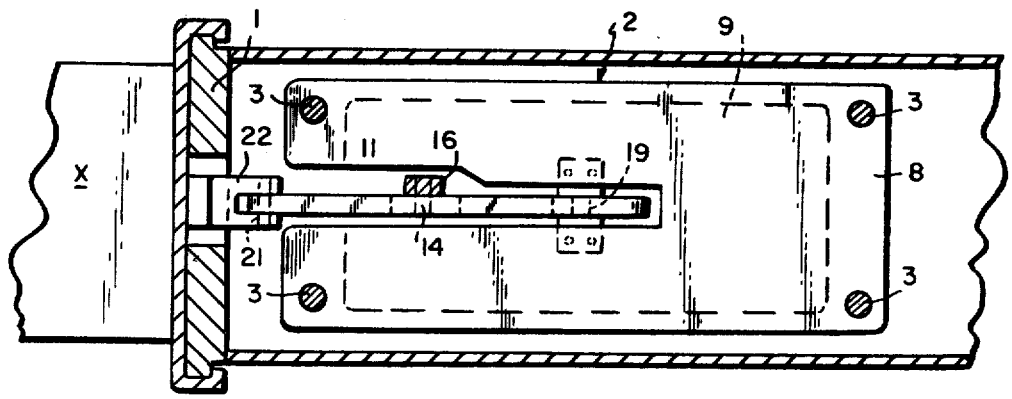
FIG. 3 is a plan view of a counterweight in the system.

The X-ray apparatus in FIG. 1 comprises a support including an L-shaped base L with a horizontal arm La swinging on a pivot assembly P, and an upright arm Lb extending at right angles to the horizontal arm. At the upper end of the upright arm Lb is a heavy bearing B in which a U-shaped part of the support rotates about an axis A1. The U-shaped support part comprises a vertical arm Uc and an upper horizontal arm Ua and a lower, hollow arm Ub having upper and lower walls 4 and 6, and side walls 7. At the end of the lower arm Ub is a housing X for an X-ray tube which is a radiation source. At the end of the upper arm Ua is a radiation receptor, namely a radiation image intensifier II which electronically intensifies the X-ray image and projects the intensified image on a beam splitter BS allowing the image to be recorded or transmitted by a still camera SC, a motion picture camera MC and a television camera TV. Below the image intensifier II is another radiation receptor such as a film holder or changer FC. The image intensifier II and X-ray tube define a radiation axis A2 which intersects the axis A1 of the U-shaped support part U at an isocenter C. The isocenter C is also the location of the subject of radiological examination. The subject is usually a patient lying on a table T which slides on rails R supported on a standard S.

The radiation source housing X and the two radiation receptors II and FC are slidingly mounted on the upper and lower arms Ua and Ub respectively so that they can be moved up and down along the radiation axis A2. The film changer FC can also move transversely of the guides G out of the way of the image intensifier so that either the film changer or image intensifier can be the active radiation receptor. To keep the image intensifier close to the radiation image plane it is desirable to move the image intensifier together with the film changer even though the image intensifier is not active as a radiation receptor.

The X-ray tube housing X is guided in its reciprocation along the radiation axis A2 by tracks 1 at the free end of the lower support arm Ub. A counterweight 2 for the X-ray tube and housing X slides on four vertical guide rods 3 which are anchored to the upper wall 4 and lower wall 6 of the arm Ub. The counterweight 2 comprises a steel frame 8 holding a lead core 9. A first order lever 11 has a medial slot 12 which slides on the roller 13 of a fulcrum 14. The fulcrum 14 is supported on a hanger 16 depending from the upper wall 4 of the lower support arm Ub. The counterweight end of the lever forms a fork 17 sliding on the roller 18 of a pivot 19 anchored at the center of gravity of the counterweight. The other end of the lever 11 is attached by a pivot pin 21 to a bracket 22 attached to the X-ray tube housing X.

With the lever slidingly connecting the X-ray tube housing X and the counterweight 2 the X-ray tube housing is very closely counterbalanced in all up and down positions of the counterweight transversely of the upper and lower walls 4, 6 of the arm Ub. The X-ray tube counter balancing system is entirely adjacent the free end of the arm Ub and is directly connected to the X-ray tube housing rather than being connected by cables to counterweights in the vertical arm Uc as in previous systems. This compact localized counterweight system does not interfere or compete for space with counterweight systems for the radiation receptors II and FC. It should be noted that in the horizontal arm Ub the guide means for the X-ray tube housing X and the counterweight 2, namely the tracks 1 and the guide rods 3, guide the housing and counterweight on parallel (vertical) paths. Ordinary fixed pivots for the lever 11 would not allow such movement but the fulcrum 14 and pivot 19 are slidingly engaged by the lever allowing the effective lever length to change, but without changing the half lever length to either side of the fulcrum, i.e. the leverage ratio.

It should be understood that the present disclosure is for the purpose of illustration only and that this invention includes all modifications and equivalents which fall within the scope of the appended claims.

We claim:

1. Radiological apparatus comprising:
   a support; and
   radiation source means and radiation receptor means at spaced positions on the support for examination of a subject at a location therebetween, the source and receptor means having a common radiation axis extending through the subject location, and each means being mounted on the support to move along the radiation axis;
   wherein the support includes
   an arm extending to one radiation means toward the radiation axis;
   means on the arm guiding the radiation means along the radiation axis;
   fulcrum means on the arm;
   a lever pivoted on the fulcrum means and pivotally attached at one end to the radiation means; and
   a counterweight guided on the arm and engaging the other end of the lever to counterbalance the radiation means.

2. Apparatus according to claim 1 wherein the support is U-shaped and includes two generally parallel arms, the radiation means being mounted on respective arms.

3. Apparatus according to claim 2 wherein one arm is hollow and the counterweight is contained within the arm.

4. Aparatus according to claim 3 wherein the hollow arm is horizontal.

5. Apparatus according to claim 1 or 3 wherein the counterweight is guided transversely of the arm.

6. Apparatus according to claim 1 wherein the fulcrum makes sliding engagement with the lever.

7. Apparatus according to claim 1 wherein the counterweight slidingly engages the lever.

8. Apparatus according to claim 1 including means guiding the radiation means and counterweight on parallel paths, wherein the fulcrum, the lever attachment to the radiation means and the lever engagement with the counterweight constitute pivots, two of which are sliding pivots.

* * * * *